United States Patent [19]

Mizumoto

[11] 4,390,012
[45] Jun. 28, 1983

[54] RIGID TYPE ENDOSCOPE

[75] Inventor: Morihide Mizumoto, Hachioji, Japan

[73] Assignee: Olympus Optical Co., Ltd., Tokyo, Japan

[21] Appl. No.: 139,724

[22] Filed: Apr. 14, 1980

[30] Foreign Application Priority Data

Apr. 17, 1979 [JP] Japan .................. 54-46813

[51] Int. Cl.³ .............................. A61B 1/00
[52] U.S. Cl. ............................ 128/4; 350/96.26
[58] Field of Search .................. 128/4–9; 350/96.15, 96.2, 96.26

[56] References Cited

U.S. PATENT DOCUMENTS

| | | | |
|---|---|---|---|
| 4,063,796 | 12/1977 | Hiltebrandt | 128/4 X |
| 4,176,909 | 12/1979 | Prunier | 350/96.2 |
| 4,182,547 | 1/1980 | Siegmund | 128/4 |

FOREIGN PATENT DOCUMENTS 1961773  7/1970  Fed. Rep. of Germany .

*Primary Examiner*—Stephen C. Pellegrino
*Attorney, Agent, or Firm*—Frishauf, Holtz, Goodman and Woodward

[57] ABSTRACT

A rigid type endoscope comprises an ocular and a rigid optic tube. The proximal end portion of the optic tube is inserted in a hollow connecting member connected to the ocular. An elastic holding mechanism is disposed between the connecting member and the proximal end of the optic tube for elastically holding the proximal end portion of the optic tube in the ocular. A transverse force exerted on the optic tube inserted in an object to be observed is distributed over the entire length of the proximal end portion of the optic tube by the elastic holding mechanism, thereby preventing the optic tube from being broken or permanently bent.

14 Claims, 14 Drawing Figures

RIGID TYPE ENDOSCOPE

BACKGROUND OF THE INVENTION

This invention relates to a rigid type endoscope wherein a rigid optic tube is connected to an ocular part in such a manner that it is elastically swingable, when a transverse force is exerted on it, in the direction of this force.

In a conventional rigid type endoscope, such as a rigid type endoscope for medical treatment and observation of a body cavity such as a coeliscope or an industrial rigid type endoscope for observing the interior of machinery and devices without disassembly, the proximal end of the optic tube is securely fixed to an ocular part.

In inserting an endoscope of this type into an object to be observed by manipulating it at the ocular, the endoscope is forced into the object or the optic tube is forced to swing. Thus, the optic tube strikes the inner wall of the object to be observed, often producing vignette or distortion, permanently bending the optic tube, or breaking the optic tube at its proximal end. Further, these troubles are hard to detect. Especially when the outer diameter of the optic tube is small, the bending and breaking tend to occur more often.

SUMMARY OF THE INVENTION

The object of this invention is to provide a rigid type endoscope wherein the proximal end of the optic tube is elastically connected to the ocular so that the optic tube can be swung when a transverse force is exerted on it, thereby overcoming the above-mentioned difficulties.

A rigid type endoscope according to this invention has an ocular and an optic tube. Secured to the distal end of the ocular is a substantially cylindrical connecting member into which the proximal end of the optic tube is inserted. An elastic holding means is provided between the connecting member and the proximal end of the optic tube for elastically connecting the optic tube to the connecting member.

When a transverse force is exerted on the optic tube, the optic tube swings in the direction of this force against the elastic force of the elastic holding means. In swinging in this manner, excessive stress is not exerted on the optic tube, since the proximal end of the optic tube is held by the elastic holding means. Thus, the optic tube would neither be broken nor bent permanently.

BRIEF DESCRIPTION OF THE DRAWING

This invention can be fully understood from the following detailed description with reference to the accompanying drawings in which:

In FIGS. 2 to 5, 7, 9 and 11, the optical systems are omitted for simplicity.

DETAILED DESCRIPTION OF THE PREFERRED EMBODIMENTS

Figure 1:
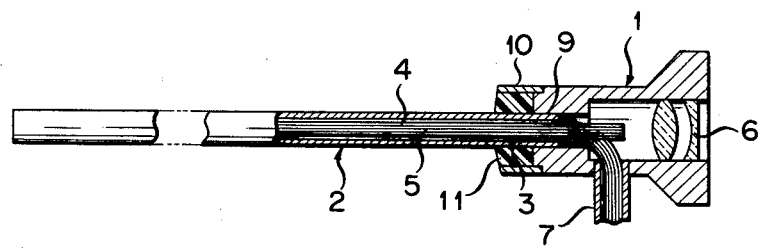
FIG. 1 is a side view in section illustrating an embodiment of a rigid type endoscope of the invention with its main part broken.

Referring to FIGS. 1 to 4, a rigid type endoscope comprises an ocular 1 and a rigid optic tube 2 with its proximal end 9 inserted into the ocular 1. The optic tube 2 is made of stainless steel or brass. In its distal end is disposed an objective (not shown). An observation relay lens 4 extends in the optic tube 2 from the objective to an ocular lens 6 disposed in the ocular 1. An illumination optical fiber bundle 5 extends through the optic tube 2 and protrudes from the lateral wall of the ocular 1 through an extension tube 7 to a light source (not shown). The above-mentioned optical system is the same type as that of a conventional rigid type endoscope and does not constitute an essential part of this invention, further explanation being omitted.

Figure 2:
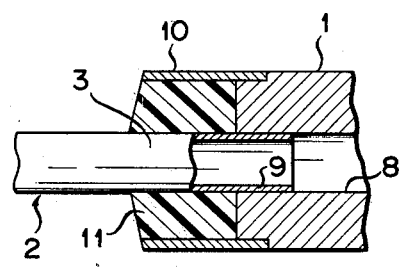
FIG. 2 is an enlarged longitudinal cross-sectional view of the main part of FIG. 1.

As best shown in FIG. 2, a cylindrical connecting member 10 made of metal such as stainless steel or brass is securely mounted on the distal end of the ocular 1 by press fit or by an adhesive. A central hole 8 is formed in the ocular part 1 so as to be aligned with the optical axis of the ocular lens 7 and coaxial with the connecting member 10. The proximal end 9 of the optic tube 2 is inserted into the distal end of the central hole 8 and is fixed thereto by press fit or a suitable adhesive. The connecting member 10 is filled with a ring shaped holding member 11 made of elastic material such as natural rubber, synthetic rubber, elastic plastic material, or the like. The inner wall of the holding member 11 elastically presses the outer surface of the proximal end portion 3 of the ocular 1 adjacent to the distal end 9 thereof. The elastic holding member 11 is preferably adhered to the connecting member 10 by an adhesive so that it will not be easily pulled out from the connecting member 10.

Figure 3:
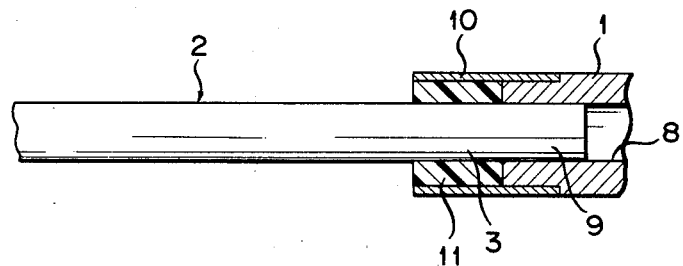
FIGS. 3 and 4 are views illustrating the positional relation between the optic tube and the ocular of FIG. 1 when a transverse force is not exerted on the optic tube, and when it is exerted on the same, respectively.

There will now be described the operation of the embodiment. When no external force is applied, the optic tube 2 inserted into an object to be observed such as a human body cavity or the interior of machinery remains straightened, as shown in FIG. 3.

Figure 4:
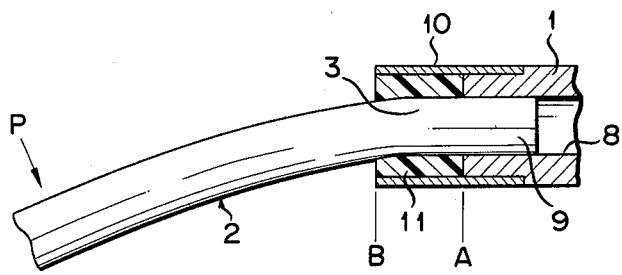

However, as seen in FIG. 4, when the optic tube 2 strikes an inner part of the object or its side wall and is applied with a transverse force P, the optic tube 2 is pressed to be bent in this direction. Since the holding member 11 is elastic, the proximal end portion 3 of the optic tube 2 is not exerted with any excessive local stress from this bend. The bending force is rather received by, and distributed over, the entire length of proximal end portion 3 defined between the inner end face A and the outer end face B of the holding member 11. Thus, the optic tube 2 is neither bent or broken at its proximal end portion 3. Although the bending moment is greatest at B, the portion of the proximal end portion 3 corresponding to B is elastically pressed deep into the holding member 11 and supported by it so that no breakage or permanent bending occurs.

Figure 5:
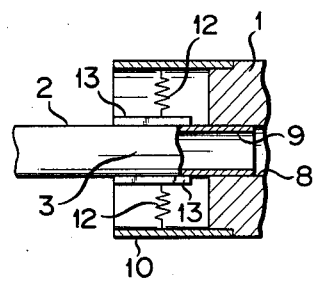
FIG. 5 is a longitudinal cross-sectional view of the main part of another embodiment of this invention.
Figure 6:
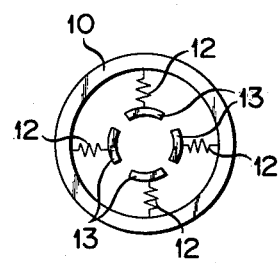
FIG. 6 is a front view of the connecting member of FIG. 5 in which elastic holding means is provided.

In the embodiment of FIGS. 5 and 6, the elastic holding member 11 in the embodiment shown in FIGS. 1 to 4 is replaced by pads 13 made of metal and having substantially the same length as the that of the proximal end portion 3 of the optic tube 2. The pads 13 are circumferentially equidistantly spaced apart on the outer surface of the proximal end portion 3. Compression coil springs 12 are disposed between the pads 13 and the inner peripheral face of the hollow cylindrical connecting member 10 for biasing the corresponding pads 13 toward the proximal end portion 3. With this construction, no local bending stress will be exerted on the proximal end portion 3 as in the embodiments shown in FIGS. 1 to 4.

Figure 7:
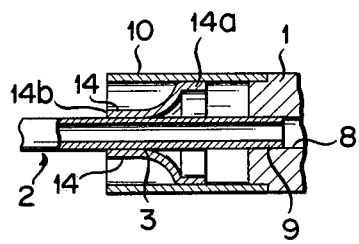
FIG. 7 is a longitudinal cross-sectional view of the main part of still another embodiment of this invention.
Figure 8:
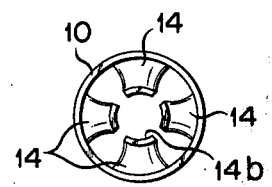
FIG. 8 is a front view of the connecting member of FIG. 7 in which elastic holding means is provided.

In the embodiment shown in FIGS. 7 and 8, plate springs 14 are disposed circumferentially on the proximal end portion 3 of the optic tube 2 instead of the elastic holding member 11 of the embodiment of FIGS. 1 to 4. One end 14a of each plate spring 14 is secured to the inner peripheral face of the connecting member 10, and the other end 14b elastically biases the outer surface of the proximal end portion 3 of the optic tube 2 in the radial, inward direction.

Figure 9:
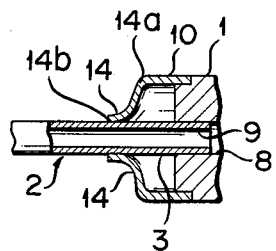
FIG. 9 is a longitudinal cross-sectional view of the main part of a further embodiment of this invention.
Figure 10:
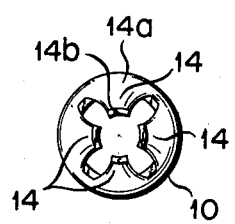
FIG. 10 is a front view of the connecting member of FIG. 9 in which elastic holding means is provided.
Figure 11:
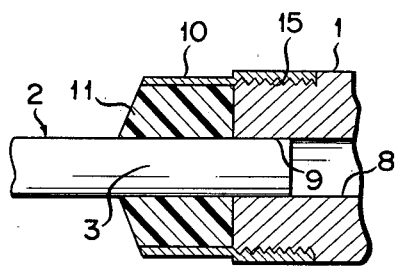
FIG. 11 is a longitudinal cross-sectional view of the main part of still another embodiment of this invention.
Figure 12:
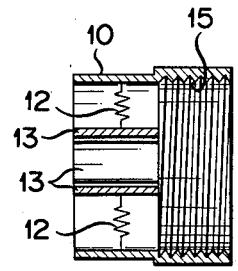
FIGS. 12 through 14 are longitudinal cross-sectional views of other embodiments in which the connecting members and the elastic holding means are integrally formed.
Figure 13:
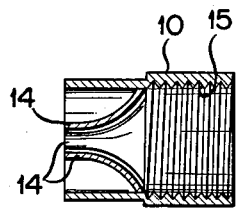
Figure 14:
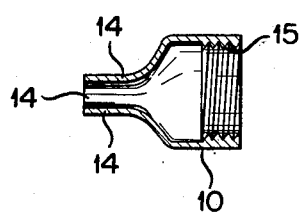

In the embodiment shown in FIGS. 9 and 10, the plate springs 14 shown in FIGS. 7 and 8 are formed integrally with the connecting member 10.

Since in any of the embodiments of FIGS. 7 to 10, a local bending stress is not exerted on the base part 3 by the spring plates 14, the proximal end portion 3 of the optic tube 2 will not be broken or permanently bent as in the case of the embodiment of FIGS. 5 and 6.

In FIGS. 11, 12, 13 and 14, a female screw 15 is formed in the inner peripheral face of the proximal end portion of the connecting part 10 which is similar to that of the embodiments shown in FIGS. 1 to 4, FIGS. 5 and 6, FIGS. 7 and 8, FIGS. 9 except for the female screw. The female screw 15 engages a male screw formed on the outer surface of the distal end portion of the ocular 1. Thus, the optic tube 2 can be easily attached to, and detached from the ocular 1. When deteriorated, the elastic holding member 11, or the springs 12 or 14 can easily be replaced.

The elastic holding member 11, the springs 12 and the pads 13 constitute elastic holding means.

This invention enables the bending force exerted on the optic tube to be distributed over the whole length of the proximal end portion of the optic tube by the use of the elastic holding means, thereby preventing the optic tube from being subjected to any excessive local stresses.

Thus, the optic tube will not be broken or permanently bent at its proximal end portion.

The rigid type endoscope of this invention presents further advantageous effects in that, since the proximal end of the optic tube is secured to the ocular, misalignment between the optical systems of the optic tube, especially between the observation optical system and the ocular lens can be avoided to allow for correct observation of the interior of the object. In addition, these optical systems can be easily adjusted when assembled.

What is claimed is:

1. In a rigid type endoscope comprising
   an ocular having a distal end;
   a hollow substantially rigid connecting member connected to said distal end of said ocular and having an inner peripheral face; and
   a rigid cylindrical optic tube having a proximal end portion inserted in said connecting member, said connecting member surrounding said proximal end portion of said rigid cylindrical optic tube;
   the improvement comprising:
   elastic holding means disposed between said connecting member and said proximal end portion of said rigid cylindrical optic tube, said elastic holding means being elastically fixed to said rigid cylindrical optic tube and being supported by said connecting member, and making a close, elastic, area-to-area contact with both the outer surface of said proximal end portion of said rigid cylindrical optic tube and with said inner peripheral face of said connecting member, for elastically holding said proximal end portion of said rigid cylindrical optic tube, whereby bending stress applied to said rigid cylindrical optic tube is widely distributed along said area-to-area contact surfaces.

2. A rigid type endoscope as claimed in claim 1, wherein said elastic holding means comprises an elastic holding member.

3. A rigid type endoscope as claimed in claim 1, wherein said holding means comprises spring means for pressing said proximal end portion of said optic tube radially inward.

4. A rigid type endoscope as claimed in claim 3, wherein said spring means comprise a plurality of compression coil springs arranged circumferentially of said proximal end portion of said optic tube.

5. A rigid type endoscope as claimed in claim 4, wherein said holding means further comprises pads interposed between said compression coil springs and said proximal end portion of said optic tube.

6. A rigid type endoscope as claimed in claim 3, wherein said spring means comprises a plurality of plate springs each having two ends, one end being securely fixed to said connecting member and the other end pressing said proximal end portion of said optic tube.

7. A rigid type endoscope as claimed in claim 6, wherein said plate springs are secured to the inner peripheral face of said connecting member.

8. A rigid type endoscope as claimed in claim 6, wherein said plate springs are formed integrally with said connecting member.

9. A rigid type endoscope as claimed in claim 1, wherein said connecting member is fixed to said distal end of said ocular.

10. A rigid type endoscope as claimed in claim 1, wherein said connecting member is detachably connected to said distal end of said ocular.

11. A rigid type endoscope as claimed in claim 1, wherein said elastic holding means is a generally ring-shaped member made of elastic material.

12. The rigid type endoscope as claimed in claim 1 or 11, wherein said rigid cylindrical optic tube extends through said elastic holding means and is in direct contact with said distal end of said ocular.

13. A rigid type endoscope as claimed in claim 12, wherein said ocular has an opening at the distal end thereof, and said rigid cylindrical optic tube is inserted in said opening and makes direct contact with the inner surface of said opening.

14. A rigid type endoscope as claimed in claim 11, whein said ocular has an opening at the distal end thereof for receiving said rigid cylindrical optic tube, and said rigid cylindrical optic tube is inserted in said opening in direct contact with said ocular, and wherein said rigid cylindrical optic tube is inserted in the opening of said elastic ring-shaped member in close, elastic, area-to-area contact with the inner surface of said ring-shaped member.

* * * * *